US011850366B2

(12) United States Patent
Sepke et al.

(10) Patent No.: US 11,850,366 B2
(45) Date of Patent: Dec. 26, 2023

(54) RESPIRATORY DEVICE WITH A PNEUMATIC CONVEYING LINE

(71) Applicant: Loewenstein Medical Technology S.A., Luxembourg (LU)

(72) Inventors: Heiko Sepke, Luetjensee (DE); Mohamed Salem-Cherif, Hamburg (DE); Joachim Gardein, Icod de los Vinos (ES); Henry Hahn, Hamburg (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 748 days.

(21) Appl. No.: 16/794,155

(22) Filed: Feb. 18, 2020

(65) Prior Publication Data

US 2020/0306488 A1 Oct. 1, 2020

(30) Foreign Application Priority Data

Feb. 20, 2019 (DE) .......................... 102019104332.8

(51) Int. Cl.
*A61M 16/00* (2006.01)
*A61M 16/10* (2006.01)

(52) U.S. Cl.
CPC .... *A61M 16/1005* (2014.02); *A61M 16/0003* (2014.02); *A61M 16/0051* (2013.01); *A61M 16/0066* (2013.01); *A61M 2205/183* (2013.01); *A61M 2205/3331* (2013.01); *A61M 2205/3606* (2013.01); *A61M 2205/502* (2013.01)

(58) Field of Classification Search
CPC .......... A61M 16/1005; A61M 16/0003; A61M 16/0051; A61M 16/0066
See application file for complete search history.

(56) References Cited

U.S. PATENT DOCUMENTS

| 4,059,246 A | * | 11/1977 | Anders | ................... G07D 11/10 |
| | | | | 406/110 |
| 2007/0227360 A1 | * | 10/2007 | Atlas | ................... A61M 16/101 |
| | | | | 96/121 |
| 2013/0206140 A1 | | 8/2013 | Kepler et al. | |

(Continued)

FOREIGN PATENT DOCUMENTS

| DE | 19949633 A1 * | 6/2001 | ........ A61M 16/0057 |
| EP | 1408313 A2 * | 4/2004 | ............ A61B 5/087 |
| WO | 2018074935 A1 | 4/2018 | |

*Primary Examiner* — Michael J Tsai
(74) *Attorney, Agent, or Firm* — Abel Schillinger, LLP

(57) ABSTRACT

A respiratory device comprises a housing, a user interface, and a pneumatic unit comprising at least one of each of a respiratory gas drive, a measuring unit, a control unit, and a sound unit and designed as a pneumatic conveying line forming a respiratory gas path from an appliance inlet to an appliance outlet of the housing. At least one component of the pneumatic unit or the pneumatic conveying line is removable from the housing. A cooling air path driven by a cooling fan is guided through the housing from a cooling air inlet to a cooling air outlet and at least the control unit, the respiratory gas drive and a main circuit board are arranged in the cooling air path in such a way that the component having the highest heat build-up during operation is arranged at an end of the cooling air path in a direction of flow of the cooling air path.

16 Claims, 8 Drawing Sheets

(56) References Cited

U.S. PATENT DOCUMENTS

| | | | |
|---|---|---|---|
| 2017/0082116 A1* | 3/2017 | Nibu | H01B 7/00 |
| 2017/0340847 A1* | 11/2017 | Taylor | A61M 16/205 |
| 2019/0255276 A1 | 8/2019 | Van Schalkwyk et al. | |

* cited by examiner

RESPIRATORY DEVICE WITH A PNEUMATIC CONVEYING LINE

CROSS-REFERENCE TO RELATED APPLICATIONS

The present application claims priority under 35 U.S.C. § 119 of German Patent Application No. 10 2019 104 332.8, filed on Feb. 20, 2019, the entire disclosure of which is expressly incorporated by reference herein.

BACKGROUND OF THE INVENTION

1. Field of the Invention

The present invention relates to a respiratory device comprising a housing comprising a pneumatic unit and at least one further component, in particular a respiratory gas drive and at least one measuring unit, and also an expiration unit, an accumulator, a control unit and a cooling fan.

2. Discussion of Background Information

Respiratory devices of this kind are typically attached to a supply network for power supply and are connected by a breathing tube to a breathing mask or another patient interface. A patient places the breathing mask in the facial region during ventilation.

It is known, for example, to use such respiratory devices to perform CPAP therapy, APAP therapy or bilevel ventilation. Such respiratory devices are also used in emergency therapy, cough management and in hospitals. In principle, any desired ventilation sequences can be predefined via the control system of the appliance.

It is known to operate respiratory devices/respirators with a leakage hose system, a single-hose system or a double-hose system. In order to change from a leakage hose system or a single-hose system to a double-hose system, the known respirators disclose a reconfiguration of a region of attachment of the hose system to the respirator.

When a leakage system is used, the exhaled air containing CO2 is flushed out continuously via an exhalation system. By contrast, in a valve system, the exhalation is controlled via the patient valve. In the use of the single-hose system with patient valve, the air exhaled by the patient escapes through the patient valve to the environment. The appliance controls the patient valve. In the use of the double-hose system with patient valve, an exhalation hose additionally discharges the exhaled air through the respirator into the ambient air.

It would therefore be advantageous to have available a device of the type mentioned at the outset that provides an improved quality of use.

SUMMARY OF THE INVENTION

The present invention makes available a respiratory device according to the independent claims. Developments and advantageous embodiments are the subject matter of the dependent claims. Further advantages and features will become clear from the general description and from the description of the exemplary embodiments.

The present invention relates to a respiratory device comprising a housing, a user interface and a pneumatic unit, wherein the pneumatic unit comprises at least one of each of the components respiratory gas drive, measuring unit, control unit and sound unit, wherein the pneumatic unit is designed as a pneumatic conveying line, wherein the pneumatic conveying line forms a respiratory gas path from an appliance inlet to an appliance outlet of the housing, and wherein at least one component of the pneumatic unit or the pneumatic conveying line is removable from the housing.

The present invention also relates to a respiratory device comprising a housing comprising a pneumatic unit and at least one further component, in particular a respiratory gas drive, and at least one measuring unit, and also an expiration unit, an accumulator, a control unit and a cooling fan.

The measuring unit can be a flow sensor, pressure sensor, volume sensor, gas sensor or oxygen sensor or can comprise such a sensor.

According to the invention, the pneumatic unit is designed as a pneumatic conveying line, wherein the pneumatic conveying line is formed and arranged from an appliance inlet to an appliance outlet of the housing and comprises a support frame on which are arranged at least one component, in particular the respiratory gas drive, at least one sound unit, at least one flow measurement path, at least one measuring unit and the cooling fan, wherein the pneumatic conveying line is removable from the housing. Generally, the pneumatic conveying line comprises at least the respiratory gas drive, the cooling fan and/or an oxygen unit/O2 cartridge.

The support frame is configured to receive the pneumatic conveying line comprising at least one component, in particular the respiratory gas drive, at least one sound unit, at least one flow measurement path, at least one measuring unit and at least the cooling fan. The support frame is configured to be able to be arranged in the housing in the device. Generally, the support frame is arranged at least regionally on the support frame. For example, the support frame can be screwed onto the housing, or the support frame can be designed and configured to be insertable into a receptacle of the housing.

The respiratory gas drive can be a blower, a valve, an oxygen source (high pressure) or an air pressure source (high pressure) or a combination of the aforementioned. The respiratory gas drive is, for example, arranged to oscillate freely in the pneumatic conveying line via at least two suspension points, in particular three suspension points.

The control unit of the device generally comprises at least one storage unit and an evaluation unit. The storage unit is configured to store measurement values, information items and/or parameters and to make these available for evaluations by the evaluation unit. The evaluation unit is configured to compare the measurement values, information items and/or parameters with one another or with external data. The control unit is configured to receive data from components of the device, in particular from a measuring unit of the flow measurement path, and to store and analyze said data. Optionally, the control unit is configured to transmit data, measurement values, information items and/or parameters to a digital interface of the device.

The device is also configured in particular for use in pediatric ventilation. The device comprises stored ventilation modes. In particular, the device comprises at least one high-flow mode and at least one PEEP control mode. Generally, the control unit of the device is configured to adjust the ventilation modes, frequencies, triggers and flows of the device.

The pneumatic conveying line is generally removable in one piece from the housing. The pneumatic conveying line is in this case removable from the housing together with the support frame. In one piece means that the support frame comprising the pneumatic conveying line is removable from and insertable into the housing in one. This has the advantage that the pneumatic conveying line is removable from the housing quickly and safely for maintenance and repair work.

Generally, components in particular that can be reconditioned/reused are arranged on/in the pneumatic conveying line. This has the advantage that reconditionable/reusable components are removable quickly and in one piece from the device. Typically, the pneumatic conveying line can be removed in one piece from the housing and placed in one piece into the reconditioning unit. Alternatively, the pneumatic conveying line can be removed in one piece from the housing, wherein the components are individually removable from the pneumatic conveying line in the uninstalled state. This has the advantage that the components can also be placed individually into the reconditioning unit or replaced. Generally, at least the respiratory gas drive is configured to be able to be disinfected by immersion disinfection. Optionally, the components are disposable components, or the components are configured to be able to be autoclaved, disinfected or sterilized.

The device described above has in general the advantage of permitting ventilation of a patient, wherein mobility of the patient can be maintained. For example, the device can be mounted on a wheelchair. The device moreover comprises an aspiration function and a cough mode. The device can be adapted to different hose systems without reconfiguration of the region of attachment of the hose system to the respirator. Furthermore, the above device has the advantage that it is quick and easy to clean, has a narrow construction with optional orientation, and is extremely quiet in operation by virtue of the sound units.

In a development of the invention, components are removable from the pneumatic conveying line in the state when extracted from the housing. This has the advantage that used components or damaged components are likewise quickly and easily removable individually from the device and the pneumatic conveying line. Moreover, the risk of damage to other components during maintenance work is reduced. Generally, the pneumatic conveying line has at least one non-return valve with at least one bypass.

In one embodiment, the pneumatic conveying line is mounted in the housing of the device by at least one viscoelastic or elastomeric suspension. Generally, the pneumatic conveying line comprising the support frame is mounted in the housing by at least one viscoelastic or elastomeric suspension at at least two points/regions. The viscoelastic suspension combines the functions of load bearing, soundproofing, and binding of the pneumatic conveying line or the respiratory gas drive in the housing.

In one development, the pneumatic conveying line is mounted in the contact region of the pneumatic conveying line to the housing, in particular in the region of a respiratory air outlet, a cooling air inlet and the cooling fan. This has the advantage that the regions of the pneumatic conveying line that are mounted viscoelastically are in particular those regions which, by contact with the housing or by their nature, have greater noise development or vibration development.

In a further development, the housing has a top wall, at least one bottom wall and at least two side walls, wherein the appliance inlet and the appliance outlet are formed at two non-opposite side walls of the housing. Generally, the housing has a rectangular shape. Alternatively, the housing can have a round, circular or semicircular design and any other geometric shape. Optionally, the appliance inlet and the appliance outlet are formed at two non-opposite sides of the housing. Optionally, the appliance inlet can be arranged at right angles to the appliance outlet.

The design of the appliance inlet and of the appliance outlet at two non-opposite side walls of the housing has the advantage that air flowing through the device, and intended to be delivered to the patient, can be guided along a longer path through the housing of the device, wherein multiple deflection of the air can be achieved, as a result of which noise is reduced. This contributes to a particularly quiet mode of operation of the device.

The top wall is generally configured to receive a user interface, in particular an operating and display element. The arrangement of the user interface in the region of the top wall has the advantage that the user can freely access the operating surface of the user interface.

In a further development, at least one side wall is configured as an optional bottom wall. In the embodiment of at least one side wall as an optional bottom wall, the device, in addition to the horizontal orientation on the bottom wall, can also be placed vertically on the optional bottom wall. By setting up at least one side wall as an optional bottom wall, the standing surface area of the device is made smaller and the space taken up by the device is thus reduced. Moreover, the orientation of the user interface is changed in such a way that a user can easily read and operate the device even when lying down. Generally, the optional bottom wall is a side wall that lies opposite a side wall configured to receive operating elements.

The device is also characterized in that no cooling air inlet or cooling air outlet or appliance inlet or appliance outlet is arranged in the bottom wall or in the side wall configured as optional bottom wall.

In one embodiment, the bottom wall of the housing is detachable, and the pneumatic conveying line is removable in one piece via an opening of the bottom wall. This has the advantage that only one wall of the housing of the device has to be removed in order to remove the pneumatic conveying line from the housing. This contributes to quick and simplified maintenance of the appliance.

In one development of the invention, the accumulator and the respiratory gas drive are arranged in the housing in such a way that, in an orientation of the device both on the bottom wall and also on the side wall configured as optional bottom wall, a center of gravity is formed by the accumulator and the respiratory gas drive. This has the advantage that the stability of the device can be ensured by arranging heavy components of the device in a lower region of the housing, both in an orientation on the bottom wall and in an orientation on the optional bottom wall.

In a further development, the pneumatic conveying line has at least two sound units, wherein at least one first sound unit is arranged on a suction side of the pneumatic conveying line and one second sound unit is arranged on a pressure side of the pneumatic conveying line. By providing a sound unit on the suction side and a sound unit on the pressure side of the pneumatic conveying line, development of noise in the pneumatic conveying line can be particularly effectively reduced.

Optionally, the suction side of the device comprises at least two sound units. For example, a first sound unit on the suction side can be arranged downstream from the cooling air inlet in the direction of flow, and a second sound unit on the suction side can be arranged directly upstream from the respiratory gas drive. The first sound unit of the suction side and the second sound unit of the suction side can be arranged one behind the other or separate from each other.

In one embodiment, the sound unit on the suction side is arranged at a receptacle of the respiratory gas drive and comprises a blower cap, a foam carrier, at least one absorber foam, a decoupling device and at least one foam ring. The decoupling device is configured to decouple the respiratory gas drive from the suction-side sound unit. This contributes to reduced development of noise. The suction-side sound unit generally comprises an oxygen inlet of the O2 cartridge.

The foam ring is configured to guide the respiratory air, which flows through the foam ring, in a straight line. This has the advantage that turbulence behind the blower cap is minimized and, at the same time, the airborne sound of the flow and of the respiratory gas drive is absorbed. The sound unit, with its absorber foams, forms a complex air route with multiple deflection of the air and at the same time with soundproofing.

In a further embodiment, the pneumatic conveying line is configured and arranged to guide respiratory air inside the pneumatic conveying line in such a way that different air routes can be selected for different hose systems. In particular, the device is configured to be operated with a leakage hose system, a single-hose system or a double-hose system. The device thus configured has the advantage that it is possible to switch between the individual hose systems without the device itself being reconfigured.

In one embodiment, the device forms a cooling unit, wherein the cooling unit has a cooling air inlet and a cooling air outlet, wherein a cooling air path is configured and designed between the cooling air inlet and the cooling air outlet. The cooling unit thus consists of individual components which guide a stream of cooling air along a cooling air path. The cooling air path is generally configured in such a way that it is guided freely in the housing of the device, wherein a main direction of flow of the cooling air path is generally guided from one side wall to an opposite side wall. Alternatively, the cooling air path can be guided from one side wall to a non-opposite side wall.

In one development, the cooling fan is arranged in the housing in such a way that an air stream from the cooling air inlet is guided at least via the control unit and the respiratory gas drive in the direction of the cooling air outlet. The cooling fan is generally configured to aspirate cooling air from the cooling air inlet, which is generally arranged in a side wall opposite the side wall in which the cooling fan is arranged. The cooling fan is configured in this case to guide the cooling air through the interior of the housing of the device via the individual components of the pneumatic conveying line.

The cooling fan is generally configured such that it is able to be regulated. Able to be regulated means that the speed of rotation or running speed of the cooling fan is steplessly adjustable. The cooling fan can be configured so as to be able to be regulated automatically. The cooling fan typically comprises at least one temperature sensor, wherein the cooling fan is configured so as to be able to be controlled/regulated on the basis of a temperature detected by the temperature sensor in the cooling fan or on the basis of a characteristic curve corresponding to a ventilation mode. The cooling fan is configured to aspirate cooling air/ambient air from a cooling air inlet, wherein the cooling air can be guided in a targeted manner via air baffles in the interior of the housing of the device.

In a further development, at least the control unit, the respiratory gas drive and a main circuit board are arranged in the cooling air path, wherein the control unit, the respiratory gas drive and the main circuit board are arranged in the cooling air path in such a way that the component that has the highest heat build-up during operation is arranged at the end of the cooling air path in the direction of flow of the cooling air path. This has the advantage that the heat of the components with the highest heat build-up is entrained a short distance in the cooling air path before being discharged from the housing. In this way, the heat of the control unit, of the respiratory gas drive and of the main circuit board is guided briefly within the cooling air path and discharged as quickly as possible. This contributes to particularly effective cooling of the device.

In a further embodiment, the accumulator is arranged in the cooling air path. This has the advantage that, by means of the cooling of the accumulator in the cooling air path, a process of charging the accumulator can be improved.

In a further development, the respiratory gas drive is arranged at the end of the cooling air path in the direction of flow of the cooling air path. This has the advantage that the component with the generally highest heat build-up is arranged at the end of the cooling air path. In an alternative embodiment, the accumulator is arranged at the end of the cooling air path.

Typically, the respiratory gas drive is arranged so as to oscillate freely in the housing of the device. In this way, the respiratory gas drive is mounted with acoustic decoupling in the housing, as a result of which a particularly quiet operation of the device is supported.

In one embodiment, the cooling air path is designed and configured in the opposite direction to and independent of the respiratory gas path of the pneumatic conveying line. In this way, it is possible on the one hand to achieve a space-saving arrangement of the components inside the housing. On the other hand, the warmest components of the pneumatic conveying line can in this way be arranged close to the outlet of the cooling air path, as a result of which an effective cooling of the housing is achieved.

In one development, the pneumatic unit comprises a flow measurement path which comprises at least one measuring unit and is configured to detect at least one parameter of a respiratory gas in the flow measurement path, wherein the flow measurement path is designed and configured linearly, wherein a lattice mesh is arranged at a start and/or at an end of the flow measurement path, and wherein the flow measurement path is designed to be removable and reconditionable. The measuring unit is generally configured to transmit data, values, information items and parameters to the control unit.

The flow measurement path is generally removable in one piece from the pneumatic conveying line. By virtue of the linear design of the flow measurement path, a turbulent flow of the respiratory air within the flow measurement path is prevented. The steady movement of air within the flow measurement path supports the measurement by the measuring unit in the flow measurement path. The flow measurement path comprises at least one sensor, which is configured to detect a flow of the respiratory air. Alternatively, the flow measurement path can comprise further sensors in order to detect further measurement values or parameters. For example, the flow measurement path can comprise a pressure sensor.

In a further development, the at least one measuring unit is designed and configured to be removable from the housing, wherein the at least one measuring unit comprises at least one sensor for detecting at least one parameter of the respiratory air guided via the respiratory gas path. This embodiment has the advantage that the measuring unit is replaceable. Therefore, in the case of a defective or used-up measuring unit, the measuring unit can be removed individually from the pneumatic conveying line and reconditioned or replaced.

The device can also be characterized in that the expiration unit is configured and designed to be removable from a receptacle of the housing, wherein the expiration unit comprises at least one PEEP valve having a membrane to which a control pressure can be applied in order to block or enable a respiratory gas flow via the expiration unit, and/or wherein the expiration unit has at least one tap for a flow measurement.

In one aspect of the invention, the respiratory device comprises a housing, a user interface and a pneumatic unit, wherein the pneumatic unit comprises at least one of each of the components respiratory gas drive, measuring unit, control unit and sound unit, and it is characterized in that the pneumatic unit is designed as a pneumatic conveying line, wherein the pneumatic conveying line forms a respiratory gas path B from an appliance inlet to an appliance outlet of the housing, wherein the housing has a top wall, at least one bottom wall and at least two side walls, and wherein at least one side wall is configured as an optional bottom wall, and wherein at least one relatively heavy component, such as in particular the respiratory gas drive, is arranged in the housing in such a way that, in an orientation of the device both on the bottom wall and also on the side wall configured as optional bottom wall, a center of gravity is formed by the heavy component.

In one development, the expiration unit is configured and designed to be removable from the housing, wherein the expiration unit is insertable into and removable from the housing based on a click-fit system. Generally, the expiration unit is arranged in the housing at at least one side wall. The expiration unit can be configured to be usable with a double-hose system.

In one embodiment, the expiration unit comprises at least one PEEP valve, wherein the PEEP valve comprises a first portion and a second portion, wherein the first portion and the second portion are at an angle of between 1° and 179°, in particular of between 42° and 130°, to each other. This has the advantage that the PEEP valve can be arranged in the housing in a way that saves space. In particular, a PEEP valve so configured can be arranged in the housing in such a way that the first portion is arranged at a first side wall and the second portion is arranged at a second side wall. In this way, the expiration unit can be arranged in a space-saving manner in a corner of the housing, between a first side wall and a second side wall. Generally, the PEEP valve is configured as an on/off valve. The expiration unit is designed to be integrated in the housing. The expiration unit can be removed from the device separately from the pneumatic conveying line.

In a further embodiment, the device comprises a quick-change adapter which is connected to the support frame via a rotary element, wherein the quick-change adapter is configured to be rotatable from a first position to a second position via a rotation axle of the rotary element, wherein the second position is at an angle of between 42° and 180° to the first position. The quick-change adapter can optionally be configured to receive a further component.

The quick-change adapter generally has a receptacle which is configured to receive a further component. Generally, the receptacle of the quick-change adapter has a latch system which is configured to receive and hold the further component via a latching or click-fit connection. Generally, the support frame has a receptacle which is configured to receive and movably bear a rotary element.

The quick-change adapter generally has a rotary element, wherein the quick-change adapter is movably connected to the support frame of the pneumatic conveying line via the rotary element. In particular, the rotary element is configured to engage in the receptacle of the support frame.

The device has, for example, a receptacle for a quick-change adapter and comprises a quick-change adapter which is connected to a support frame via a rotary element, wherein the quick-change adapter is configured to be pivotable in the receptacle from a first position to a second position via a rotation axle of the rotary element, wherein the quick-change adapter in the second position is pivoted out from the receptacle such that in the second position a receptacle for an O2 cartridge is accessible and an O2 cartridge can be inserted, and wherein the quick-change adapter can then be pivoted back into the receptacle, together with the O2 cartridge, to the first position. In a development of the embodiment, the quick-change adapter is configured to receive an O2 cartridge. This has the advantage that the O2 cartridge, when used up, can be easily and quickly removed from the housing via the quick-change adapter. This reduces the maintenance time. The O2 cartridge is generally arranged in the region of the bottom wall of the device. This has the advantage that the O2 cartridge is removable from the device without the pneumatic conveying line having to be removed from the device. Optionally, the quick-change adapter is configured to receive another cartridge or a device for administering medication.

In one development, the housing has a receptacle which is configured to receive the pneumatic unit, wherein the pneumatic unit is insertable into the receptacle. Generally, at least one side wall of the housing has a receptacle which is configured to receive the support frame. The receptacle can be a push-in device. The pneumatic unit is held by the attached bottom wall or bears on the latter. Optionally, the support frame is connectable to the housing via a click-fit connection or via a screw connection. This has the advantage that the support frame is anchored rigidly and firmly in the housing, such that the support frame is held unchanged in the housing even if the position of the device changes.

Optionally, the housing has at least one receptacle designed as a guide rail into which a correspondingly designed viscoelastic holding element of the support frame can be inserted/pushed. This has the advantage that the pneumatic conveying line with the support frame in the housing is mounted elastically in the housing even in the event of a change of position from the bottom wall as standing surface to the optional bottom wall as standing surface. Alternatively, at least one receptacle is designed as a bearing surface. A viscoelastic material is generally a silicone.

The device can also be characterized in that the device has a user interface configured and designed as an operating and display element, wherein the operating and display element is formed in a surface of the housing of the device, wherein the operating and display element has such a surface area that it occupies more than 45% or preferably more than 50% of the surface of the housing, in particular of the top wall.

In a further embodiment, the device has a user interface which is configured and designed as an operating and display element. Generally, the operating and display element is designed as a GUI. Generally, the GUI is designed as a touch screen. Optionally, the operating and display element comprises haptic operating elements. A haptic operating element can be arranged on the top wall or on a side wall of the device. Optionally, the operating and display element is configured in one setting to emit an acoustic or haptic acknowledgment.

In one embodiment, the operating and display element is formed in a surface of the housing of the device, in particular in the top wall, wherein the operating and display element is configured to show an image, wherein the orientation of the image depends on the selected bottom wall The operating and display element is thus configured to change an orientation of the display if the orientation of the device is changed according to a selected bottom wall. The device is generally configured to automatically change/adapt the orientation of the display according to the orientation of the device.

In one development, the operating and display element forms a complete surface of the housing, wherein the operating and display element is connected to side walls of the housing by seals, wherein at least one seal is configured and designed to receive interface elements and attachments. This has the advantage that the interface elements and attachments are mounted elastically and in a watertight manner. Optionally, the interface elements and attachments can have a viscoelastic cap. The viscoelastic caps can be formed, for example, from silicone.

In a further development, the operating and display element is configured to detect a surrounding brightness and, based on the detected surrounding brightness, to change an optical display of the operating and display element, wherein the operating and display element is configured, if the surrounding brightness detected is light, to change a color intensity or to change from a color display to a black and white display. This has the advantage that, if the surrounding brightness is light, the visibility of the display of the operating and display element can be improved.

According to the surrounding brightness that is detected, the operating and display element is configured to increase the color intensity of the display or, if the brightness is strong, to change to a black and white display. By dispensing with a color display, the increased contrast can provide better display in conditions where the surrounding brightness is strong. For example, the operating and display element can be configured to change from a color display to a black and white display in a range between 5,000 lux and 20,000 lux, in particular between 7,000 lux and 9,000 lux. This is advantageous in particular when carrying the device around, particularly outdoors. The operating and display element is configured be dimmable according to a charge state of the accumulator.

In one embodiment, the device comprises a digital interface configured to transmit detected parameters, measurement values and information items to a server or an external terminal and to receive data and information items via the interface. Optionally, the device is configured to store, analyze and/or evaluate the detected values and/or information items of the measurement path. The device can be coupled via the interface to a cough management appliance or another respirator or to a patient monitor and can exchange data.

Optionally, the device is configured to transmit the detected, analyzed and/or evaluated measurement values/parameters to an external server. The transmission can be time controlled, manually triggered (e.g. triggered at the home therapy appliance or at the server), event-controlled (e.g. upon detection of certain critical states by the therapy appliance) or a permanent transmission, at least during an ongoing therapy.

A transmission of the measurement values, parameters and information items can take place every 2 hours to 7 days, in particular every 1 to 3 days. In one embodiment, the transmission takes place at least once a day/once every 24 hours. Optionally, the interface can be configured to transmit measurement values, information items or parameters in summary by the hour or to transmit the measurement values in real time. Optionally, a transmission cycle can be freely selected by the user and/or by a care provider. The interface of the respirator can be configured to perform the transmission automatically, if appropriate repeatedly or permanently, according to one or more time intervals that are permanently programmed and/or freely input.

In the event of a data connection failing, the storage unit of the device can be configured to store the measurement values and/or the information items for at least one day, wherein the interface of the device is configured to transmit the measurement values to an external server or a terminal as soon as a data connection has been re-established.

Optionally, the device is configured such that, by way of the operating and display element, information items and values that have been manually input by the user and/or by the care provider are included in the evaluation of measurement values.

In a further embodiment, the device comprises an alarm unit with a loudspeaker which is configured to emit an alarm when incidents are detected, wherein the device comprises at least one microphone which is configured to monitor an alarm emitted by the alarm unit. This affords an additional safety function for the correct use of the respirator device.

In one embodiment, the device is configured to be able to be combined with further devices. Optionally, the device has an attachment for a nebulizer, wherein the device is configured to control an attached nebulizer via the device. The device is optionally configured to detect feedback from the nebulizer and to take this into account in the control of the nebulizer.

The device comprises attachments for a server, a patient management system, a cough management device and a sleep laboratory infrastructure. The device moreover comprises a cloud function, wherein the device is configured to transmit data to a cloud via an interface, or to an attachment for a GSM module. In one development, the device comprises an attachment for a nurse call module. The device moreover comprises at least one SpO2 and/or CO2 attachment.

In one embodiment, the cooling fan is configured such that it is able to be regulated, wherein a speed of rotation of the cooling fan is able to be regulated according to a detected temperature of at least one component. Here, able to be regulated means that the cooling fan can be switched off or is steplessly adjustable in terms of its speed of rotation. This has the advantage that the cooling fan, with a low heat build-up and a low speed of rotation, develops less noise.

In a development of the embodiment, the speed of rotation of the cooling fan can be regulated on the basis of a detected temperature of the control unit, a detected temperature of the respiratory gas drive, a detected temperature of the accumulator, a detected temperature of the main circuit board and/or a detected charging current of the accumulator. Optionally, the speed of rotation of the cooling air fan can be regulated on the basis of a combination of at least two detected temperatures of components. The temperatures are generally detected by means of temperature sensors which are arranged on the respective component to be measured.

In one embodiment, the device is configured to regulate a charging current of the accumulator. By reducing the charging current, heating of the accumulator can be reduced, as a result of which the cooling effort decreases and the noise development thus drops.

In a further embodiment, the charging current of the accumulator is able to be regulated according to a detected temperature of the accumulator, of the cooling fan or at least of one further component of the device. The temperatures are generally detected by means of temperature sensors which are arranged on the respective component. A detected temperature at which the charging current is adjusted downward generally lies between 30° C. and 47° C., in particular between 35° C. and 42° C.

The present invention further relates to a quick-change adapter for a respiratory device, comprising a housing comprising at least one pneumatic unit and at least one support frame.

According to the invention, the quick-change adapter is connected to the support frame via a rotary element, wherein the quick-change adapter is configured to be rotatable from a first position to a second position via a rotation axle of the rotary element, wherein the second position is at an angle of between 42° and 180° to the first position. The quick-change adapter generally has a receptacle which is configured to receive a further component. Generally, the receptacle of the quick-change adapter has a latch system which is configured to receive and hold the further component via a latching or click-fit connection. Generally, the support frame has a receptacle which is configured to receive and movably bear a rotary element. Generally, the quick-change adapter is movably connected to the support frame of the pneumatic conveying line via the rotary element. In particular, the rotary element is configured to engage in the receptacle of the support frame.

In one embodiment, the quick-change adapter is configured to receive an O2 cartridge.

This has the advantage that the O2 cartridge, when used up, can be easily and quickly removed from the housing via the quick-change adapter. This reduces the maintenance time of the device. Generally, the O2 cartridge is arranged in the region of the bottom wall of the device. This has the advantage that the O2 cartridge is removable from the device without the pneumatic conveying line having to be removed from the device. O2 stands for oxygen. Optionally, the quick-change adapter is configured to receive another cartridge or a device for administering medication.

The present invention further relates to a flow measurement path for a respiratory gas drive.

According to the invention, the flow measurement path comprises at least one measuring unit and is configured to detect at least one parameter of a respiratory gas in the flow measurement path, wherein the flow measurement path is designed and configured linearly, wherein a lattice mesh is arranged at a start and/or at an end of the flow measurement path, and wherein the flow measurement path is designed to be removable and reconditionable.

BRIEF DESCRIPTION OF THE DRAWINGS

Preferred exemplary embodiments of the invention are explained in more detail below on the basis of highly simplified schematic drawings, in which.

In the figures, the same design elements in each case have the same reference numbers.

DETAILED DESCRIPTION OF EXEMPLARY EMBODIMENTS OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
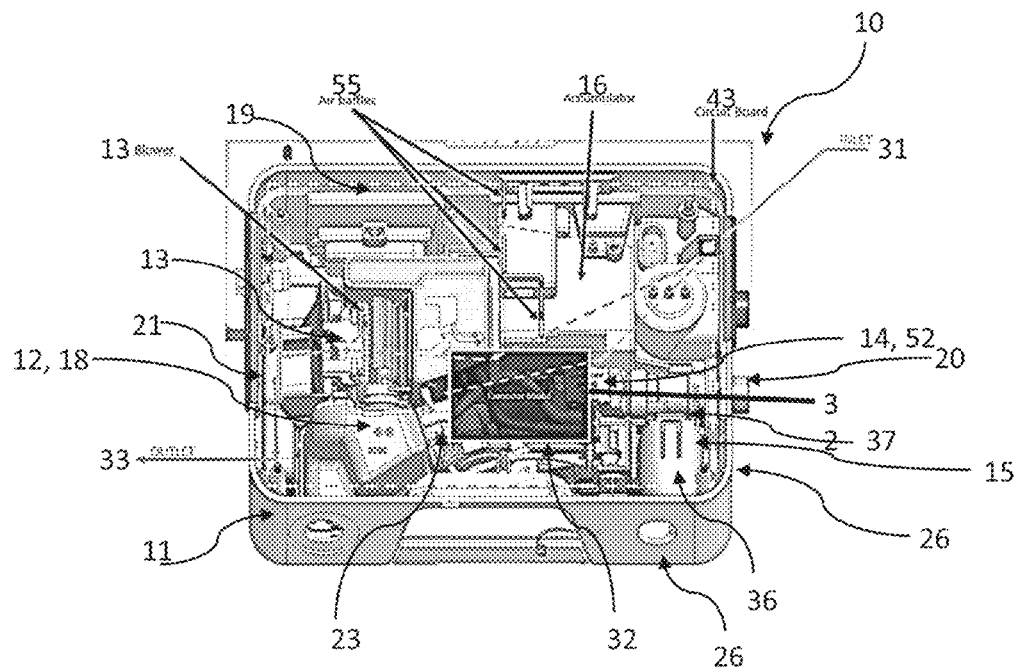
FIG. 1 shows a perspective plan view of an arrangement of components in a housing of a respiratory device according to the invention, seen from above (top wall)

FIG. 1 shows a perspective plan view of an arrangement of components in a housing 11 of a respiratory device 10 according to the invention, seen from above. Here, from above means a perspective view of an opened (not shown) top wall of the device 10. The respiratory device 10 comprises at least two side walls 26 and a top wall and (likewise not shown) a bottom wall. At least one of the side walls 26 can be configured as an optional bottom wall.

A pneumatic unit 12, comprising a support frame 21 and at least one further component, is shown in the housing 11. A component here can be in particular a respiratory gas drive 13, at least one measuring unit 14, an expiration unit 15, an accumulator 16, a control unit 32 and/or a cooling fan 17.

The pneumatic unit 12 is designed as a pneumatic conveying line 18, wherein the pneumatic conveying line 18 is formed from an appliance inlet 19 to appliance outlet 20 of the housing 11. The pneumatic conveying line 18 comprises the support frame 21 on which the at least one component is arranged. The pneumatic conveying line 18 is removable from the housing 11.

The pneumatic conveying line 18 additionally comprises at least one flow measurement path 23, wherein at least one sensor 52 is arranged in the flow measurement path 23 and is configured to detect at least one value/parameter of the respiratory air guided through the pneumatic conveying line 18. Components are removable from the pneumatic conveying line 18 in the state when withdrawn from the housing 11.

An expiration unit 15 is also shown. In the present embodiment, the expiration unit 15 is arranged in a corner region of the housing 11. The expiration unit 15 can be arranged in a side region/at one of the side walls 26 of the housing 11. The expiration unit 15 is removable from the housing 11, wherein the expiration unit 15 is insertable into and removable from the housing 11 based on a click-fit system. The expiration unit 15 comprises a PEEP valve, wherein the PEEP valve comprises a first portion 36 and a second portion 37, wherein the first portion 36 and the second portion 37 are at an angle of between 1° and 179°, in particular of between 42° and 130°, to each other.

Figure 2:
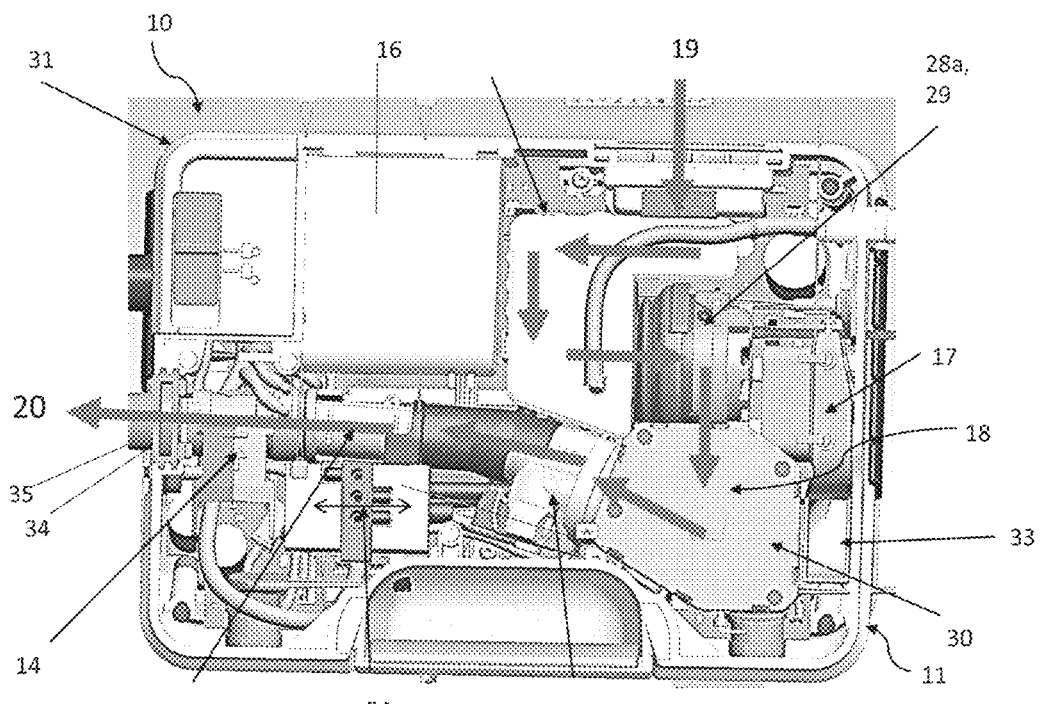
FIG. 2 shows a perspective view of an arrangement of components in the housing (shown in FIG. 1) of the respiratory device according to the invention, seen from below (bottom wall)

FIG. 2 shows a perspective view of an arrangement of components in the housing (shown in FIG. 1) of the respiratory device 10 according to the invention, seen from below. Here, from below means a view of an (opened) bottom wall of the device 10. Generally, the bottom wall is configured to be removable, such that the pneumatic conveying line 18 described in FIG. 1 is removable from the housing 11 via the opened bottom wall. The pneumatic conveying line 18 is mounted in the housing 11 of the device 10 by at least one viscoelastic or elastomeric suspension 34 shown in FIG. 2. A viscoelastic material can be a silicone. The pneumatic conveying line 18 is mounted in the contact region of the pneumatic conveying line 18 to the housing 11, in particular in the region of the respiratory air outlet 35, the cooling air outlet 31 and the cooling fan 17.

The pneumatic conveying line 18 has a suction side 29 and a pressure side 30, wherein the pneumatic conveying line 18 additionally comprises at least one suction-side sound unit 28a, 28b and also a pressure-side sound unit 28c. A suction-side sound unit 28b can be formed, for example, directly at the appliance inlet 19. For example, a sound unit 28b of this type (not shown) can be designed as an air baffle.

FIG. 2 also shows a non-return valve with bypass 53, a pressure build-up valve 54, a flow measurement path 23 and a quick-change adapter 14. The accumulator 16 is also shown.

Figure 3:
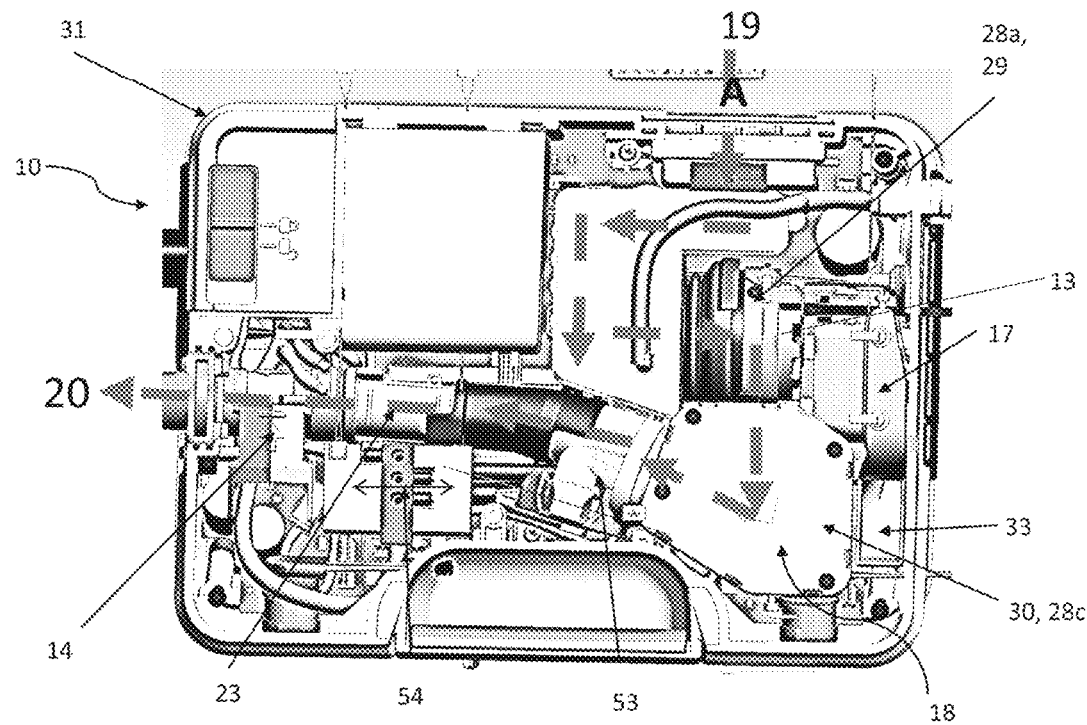
FIG. 3 shows a perspective view of a respiratory gas path A according to the invention in a pneumatic unit of the respiratory device shown in FIG. 1 and FIG. 2.

FIG. 3 shows a perspective view of a respiratory gas path A according to the invention of a pneumatic conveying line 18 of the respiratory device shown in FIG. 1 and FIG. 2. The respiratory gas path A extends from an appliance input 19 to an appliance output 20 of the device 10. The respiratory gas path A comprises the pneumatic conveying line 18 with the respiratory gas drive 13 and the sound units 28a and 28c. Moreover, the respiratory gas path comprises the flow measurement path 23 and at least one sensor. The respiratory gas drive 13 generates a suction, such that ambient air is drawn into the device 10 via the appliance inlet 19. The respiratory gas path A is configured to guide respiratory air from the environment to a patient. The sound units 28a and 28c permit a noise reduction in the air stream.

In a further embodiment (not shown), the respiratory gas path A comprises a further air deflection device 28b, which is configured to introduce the air generated with the respiratory gas drive into the device counter to the suction direction of the air stream.

Figure 4:
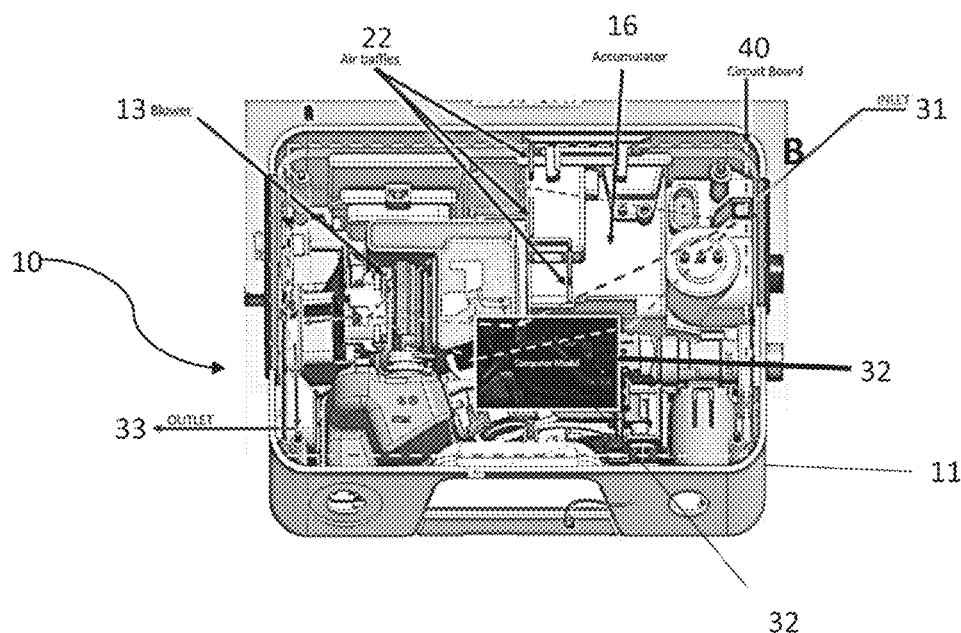
FIG. 4 shows a perspective view of a cooling air path B according to the invention in the respiratory device shown in FIG. 1 and FIG. 2.

FIG. 4 shows a perspective view of a cooling air path B according to the invention of the respiratory device 10 shown in FIG. 1 and FIG. 2. The cooling air path B extends from a cooling air inlet 31 to a cooling air outlet 33. Cooling air/ambient air is sucked for cooling into the device 10 by a cooling fan 17, which is arranged at the cooling air outlet 33.

The cooling air is guided/channeled via air baffles 22 in the housing 11. The air baffles 22 are arranged in such a way that the cooling air in the housing 11 is guided via at least the respiratory gas drive 13, the control unit 32 and the main circuit board 40. The component that has the highest heat build-up during operation is arranged at the end of the cooling air path B in the direction of flow of the cooling air path. In this way, the heat of the components with the highest heat build-up is entrained only a short distance in the cooling air path before being discharged from the housing 11. In this way, the heat of the control unit 32, of the respiratory gas drive 13 and of the main circuit board 40 is guided briefly in the cooling air path B and discharged as quickly as possible.

Figure 5:
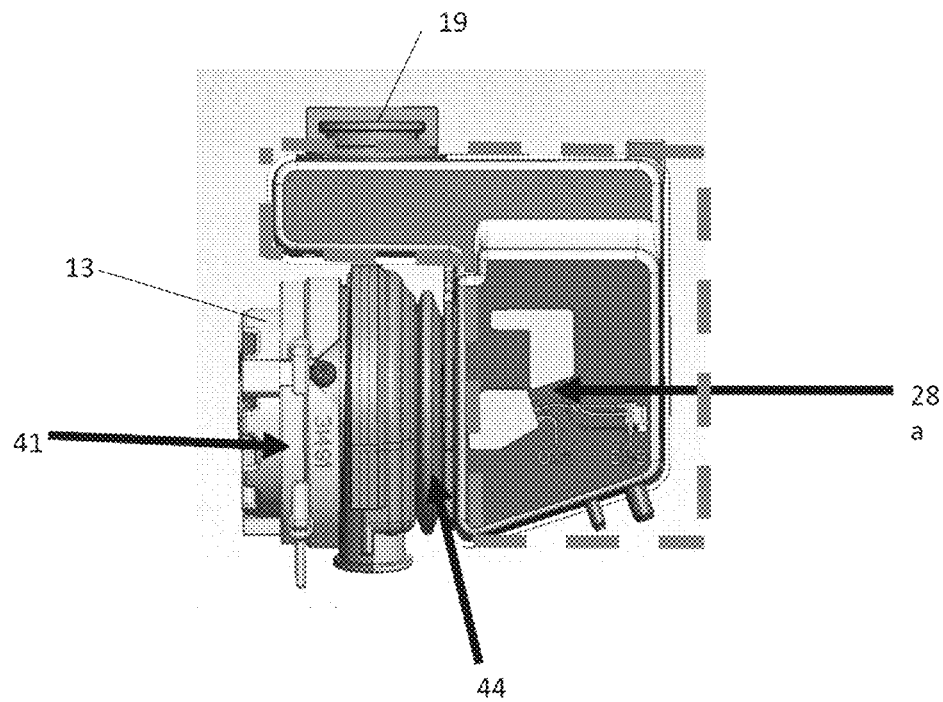
FIG. 5 shows a longitudinal section through a suction-side sound unit, with a part of the respiratory gas path of the respiratory device according to the invention.

FIG. 5 shows a longitudinal section through a suction-side sound unit 28a with a part of the respiratory air path A of the respiratory device according to the invention. The suction-side sound unit 28a is arranged downstream from the appliance inlet 19 in the air flow direction. The figure shows the appliance inlet 19, a decoupling device 44 and a blower cap 41. The suction-side sound unit 28a is configured to reduce a noise level of the respiratory air guided through the respiratory gas path B. The blower cap 41 is configured to be attachable to the respiratory gas drive 13. Thus, the suction-side sound unit 28a can be joined to the respiratory gas drive 13 in a modular fashion.

Figure 6:
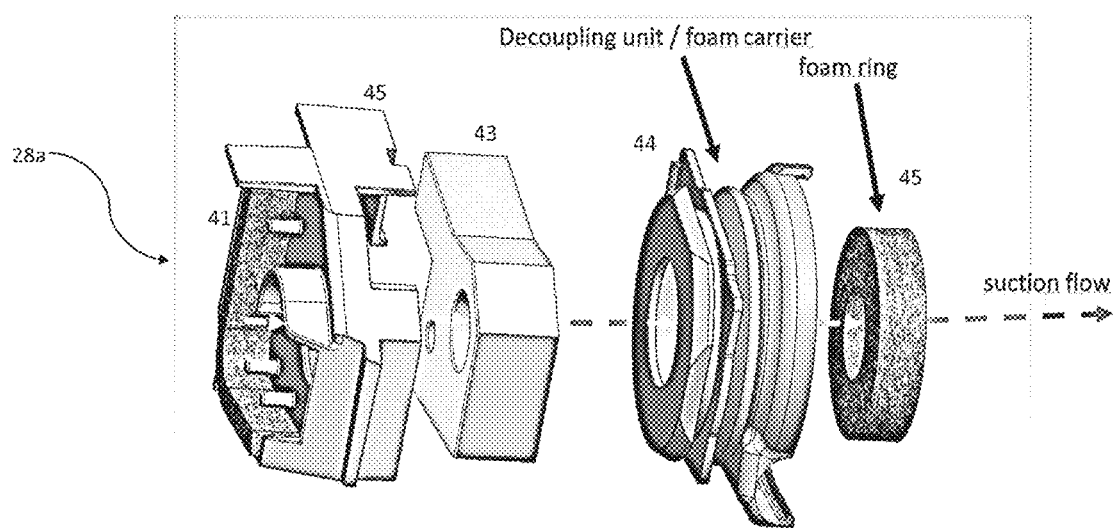
FIG. 6 shows an exploded view of the suction-side sound unit (shown in FIG. 5) of the respiratory device.

FIG. 6 shows an exploded view of the suction-side sound unit 28 (shown in FIG. 5) of the respiratory device 10. It depicts the blower cap 41 shown in FIG. 5, a foam carrier 42, an absorber foam 43, the decoupling device 44 and a foam ring 45. The foam carrier 42 is configured to receive and hold the absorber foam 43. The decoupling device 44 is generally made from a viscoelastic material, in particular from a silicone.

Figure 7:
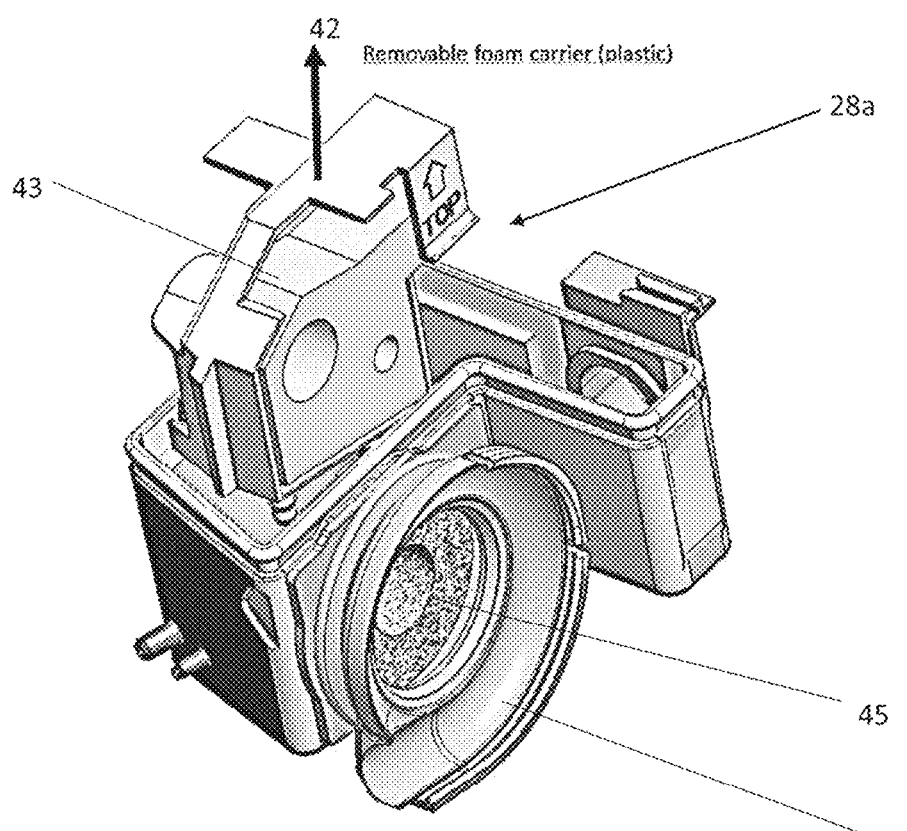
FIG. 7 shows a further exploded view of the sound unit shown in FIG. 5 and FIG. 6.

FIG. 7 shows a further exploded view of the sound unit 28a shown in FIG. 5 and FIG. 6. It shows how the foam carrier 42 with the absorber foam 43 is removable from the sound unit 28a. This is particularly advantageous, since the foam carrier 42 with the absorber foam 43 can be removed individually from the sound unit and reconditioned.

Figure 8:
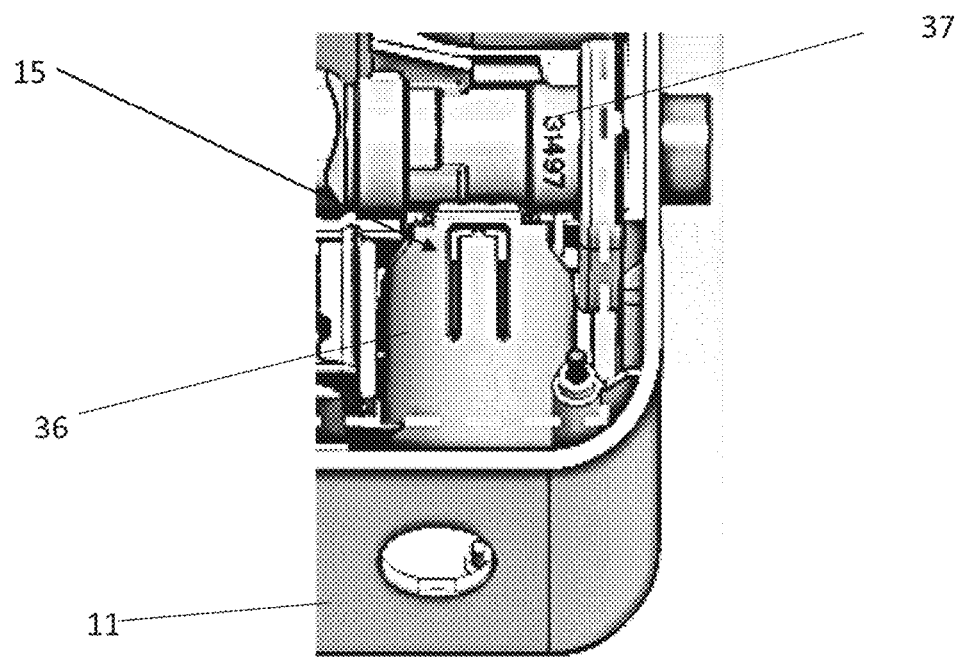
FIG. 8 shows a perspective view of an expiration unit with a PEEP valve of the respiratory device according to the invention shown in FIG. 1 and FIG. 2.

FIG. 8 shows a perspective view of an expiration unit 15 with a PEEP valve of the respiratory device 10 according to the invention shown in FIG. 1 and FIG. 2. The expiration unit 15 is configured and designed to be removable from the housing 11, wherein the expiration unit 15 is inserted into the housing 11 on the basis, for example, of a click-fit system. By means of the click-fit system, the expiration unit 15 can be removed particularly quickly from the housing 11 and reconditioned or renewed. In the present embodiment, the expiration unit 15 is rectangular, i.e. a first portion 36 of the expiration unit 15 and a second portion 37 of the expiration unit 15 are at an angle of between 1° and 179°, in particular of between 42° and 130°, to each other. Generally, the PEEP valve is configured as an on/off valve. The inlet of the expiration unit is generally formed upstream from the flow measurement path.

Figures 8A, 8B, 8C:
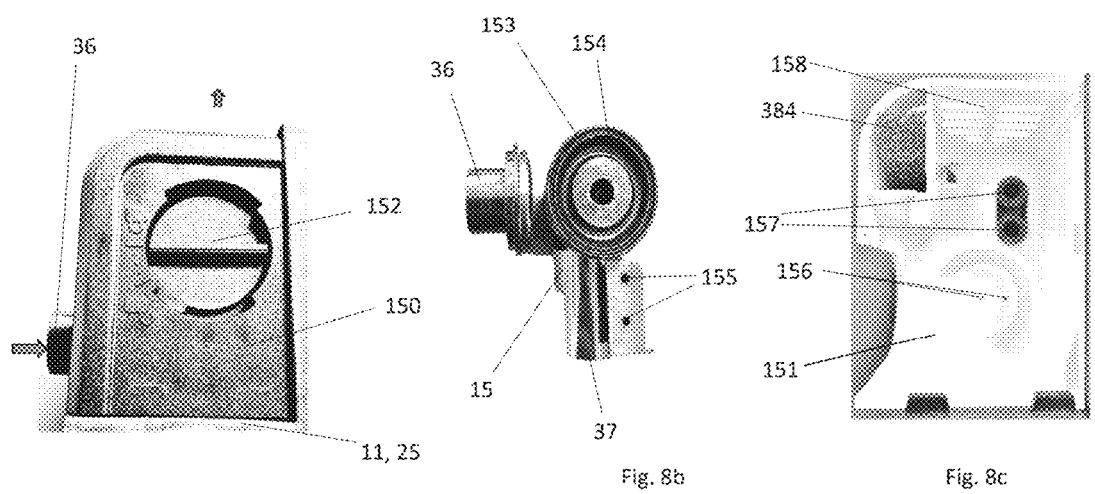
FIG. 8a shows the underside of the housing of the device according to the invention.
FIG. 8b shows the expiration unit of the device according to the invention with a PEEP valve.
FIG. 8c shows a receptacle for the expiration unit shown in FIG. 8b.

FIG. 8a shows the underside 25 of the housing 11 of the respiratory device 10. A cover 150 closes the receptacle 151 for the expiration unit 15. The cover has a quick-release closure 152, which functions as a twist lock, for example. A first portion 36 of the expiration unit serves as a connector piece for the expiration hose via which exhaled air (arrow) is guided to the expiration unit. After passing through the expiration unit (with flow measurement path), the exhaled air leaves the expiration unit (at an angle of about 90°) via the second portion 37.

FIG. 8b shows the expiration unit 15 with the PEEP valve 153, which can enable or block the flow of respiratory gas via the expiration unit 15. For this purpose, the PEEP valve 153 has a membrane 154 to which a control pressure can be applied in order to block or enable respiratory gas flow via the expiration unit 15. Two taps 155 for the flow measurement are located at the second portion 37.

FIG. 8c shows the receptacle 151 for the expiration unit 15. A receptacle for the membrane 154 is located here, wherein two passages 156 for the control pressure are arranged in the receptacle. When the expiration unit 15 is in the receptacle 151, the control pressure (generated via the blower) can be conducted through the passages 156 to the membrane. The receptacle 151 moreover has two flow passages 157 via which the flow of expiration gas, which flows through the expiration unit 15, can be measured. The flow sensor lies inside the housing. The flow passages 157 are arranged such that the taps 155 of the expiration unit 15 lie directly above the flow passages 157 (when the expiration unit 15 is in the receptacle), and a substantially leak-tight connection from the expiration unit 15 to the flow sensor is ensured. The flow of expiration gas leaves the receptacle through the expiration opening 158. For example, the expiration opening 158 is arranged facing away from the first portion 36 and facing away from the appliance inlet 19.

Figure 9:
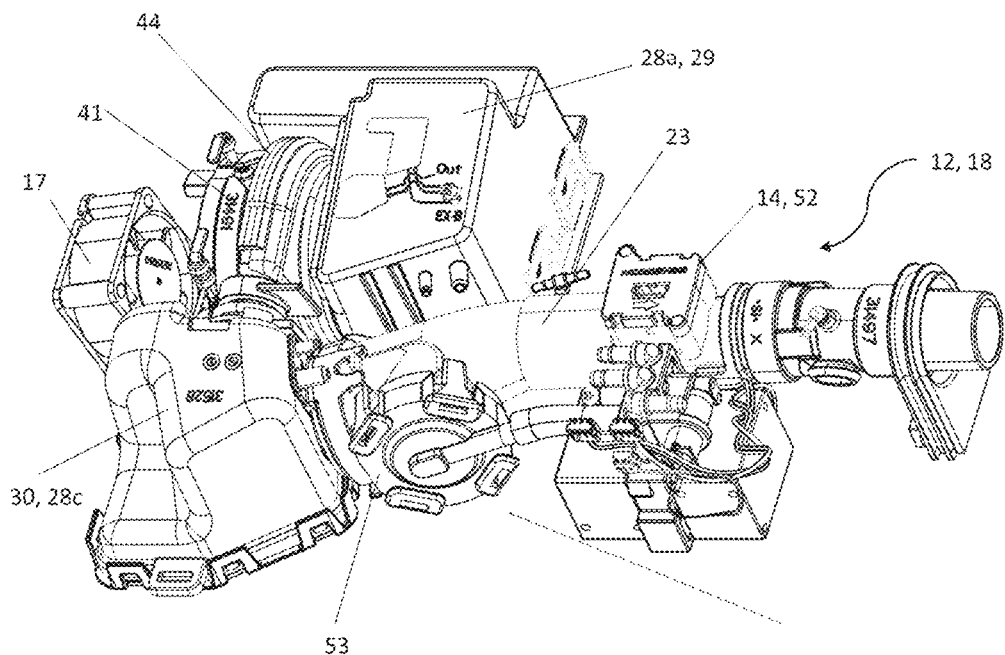
FIG. 9 shows a perspective view of a pneumatic unit of the respiratory device according to the invention.

FIG. 9 shows a perspective view of a pneumatic unit 12 of the respiratory device according to the invention. The pneumatic unit 12 in the present embodiment is designed as a pneumatic conveying line 18. Other ways of arranging and joining the components to form a pneumatic unit 12 are also conceivable. The pneumatic conveying line 18 is formed from the appliance inlet (not shown) to the appliance outlet of the housing. The pneumatic conveying line 18 comprises the support frame 21 (not shown) on which the at least one further component is arranged. The at least one further component can be in particular the respiratory gas drive, the at least one measuring unit 14, 52, the expiration unit, the accumulator, the control unit and/or the cooling fan 17. The pneumatic conveying line 18 is removable from the housing 11 in one piece comprising all of the components arranged on the support frame. The pneumatic conveying line 18 has the suction side 29 and the pressure side 30, wherein the pneumatic conveying line 18 additionally comprises at least the one suction-side sound unit 28a and the one pressure-side sound unit 28c.

The pneumatic conveying line 18 comprises as further component the flow measurement path 23, wherein the at least one sensor 52 is arranged in the flow measurement path 23 and detects at least one value/parameter of the respiratory air guided through the pneumatic conveying line 18 by the respiratory gas drive 13.

Figure 10:
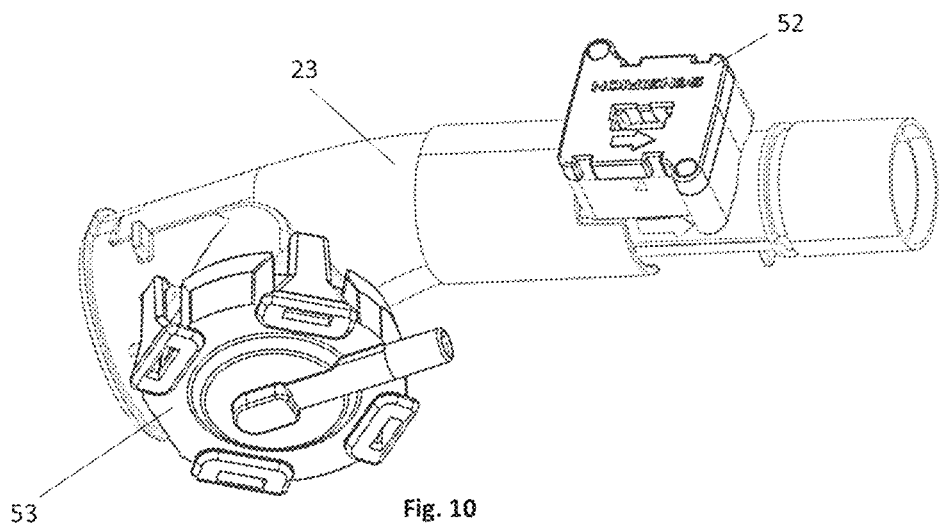
FIG. 10 shows a detail of a flow measurement path of the pneumatic unit shown in FIG. 9.

FIG. 10 shows a detail of a flow measurement path 23 of the pneumatic unit 12 shown in FIG. 9. The flow measurement path 23 is configured to detect at least one value/parameter of the respiratory air guided through the pneumatic conveying line by the respiratory gas drive. The flow measurement path 23 generally comprises at least one sensor 52, which is configured to detect a pressure and/or flow of the respiratory air in the respiratory air path B. The device is configured to store the detected values/parameters. The device is optionally configured to analyze the detected values/parameters and/or to transmit them via an interface to a server and/or a terminal. FIG. 10 also shows the bypass 53 of the non-return valve.

Figure 11:
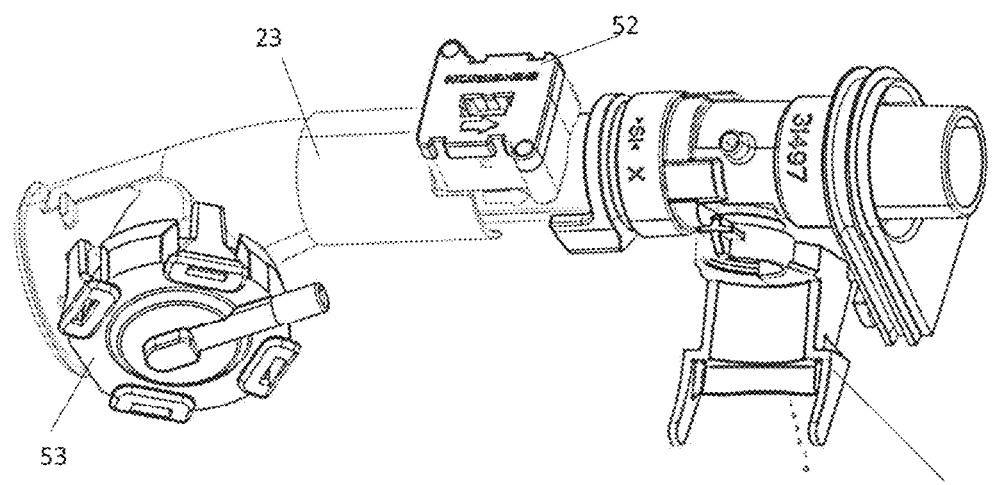
FIG. 11 shows a detail of a quick-change adapter of the respiratory device according to the invention.

FIG. 11 shows a detail of a quick-change adapter 38 of the respiratory device according to the invention. The quick-change adapter 38 is connected to the support frame via a rotary element, wherein the quick-change adapter 38 is configured to be rotatable from a first position to a second position via a rotation axle of the rotary element. The second position is advantageously at an angle of between 42° and 180° to the first position. The quick-change adapter 38 can receive a further component, in particular an O2 cartridge. For this purpose, the quick-change adapter 38 has a receptacle which is generally designed and configured corresponding to the component that is to be received. To receive the component, the receptacle has a latch/click system. FIG. 11 also shows the bypass 53 of the non-return valve, the flow measurement path 23 and the sensor 52.

Figure 11A:
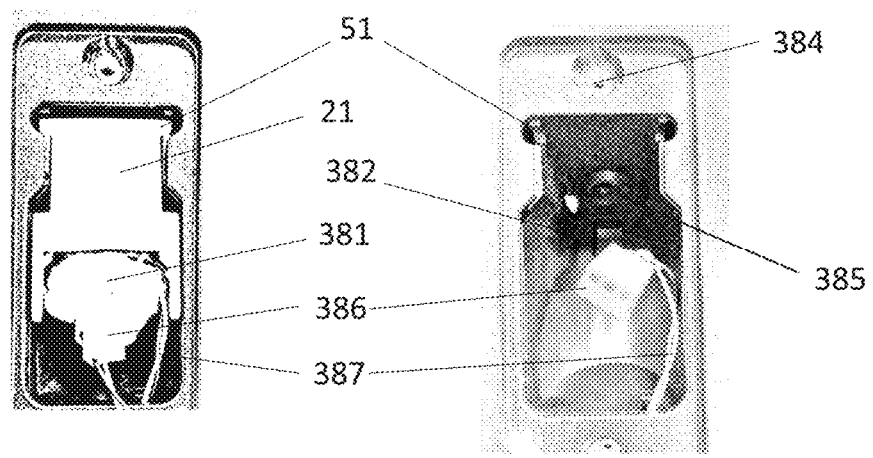
FIG. 11a shows the quick-change adapter of the device according to the invention for an O2 cartridge.

FIG. 11a shows the quick-change adapter (38) for an O2 cartridge (381). The quick-change adapter 38 can be inserted into a receptacle (382) for the quick-change adapter. The receptacle is located in the housing (11) of the device, preferably in the bottom wall (25). The bottom wall has a detachable cover for the receptacle (382), which cover is held, for example, with screws or latch elements (384). The cover is not shown here. The receptacle (382) has an access (385) to the respiratory gas stream. The access represents the pneumatic connection for the O2 cartridge (381).

The quick-change adapter (38) is connected to the support frame (21) via a rotary element (51). The support frame (21) has a receptacle (383) for an O2 cartridge. The receptacle (383) is designed such that the O2 cartridge is inserted and held there. The receptacle (383) can have a screw thread, wherein the O2 cartridge has a corresponding mating piece.

The quick-change adapter (38) is configured to be rotatable in the receptacle (382) from a first position to a second position via a rotation axle of the rotary element (51). The second position is at an angle of between 42° and 180° to the first position. In the second position, the quick-change adapter (38) is pivoted out from the receptacle (382) for the quick-change adapter. In the second position, the receptacle 383 is accessible, such that the O2 cartridge can be inserted. Together with the O2 cartridge, the quick-change adapter (38) can be pivoted to the first position into the receptacle (382). The quick-change adapter (38) latches in the first position, and the O2 cartridge is pneumatically connected via an access (385) to the gas flow, in order to determine there the oxygen content FiO2. The O2 cartridge (381) has a first end, which communicates pneumatically with the respiratory gas flow, and a second end, which is electrically connected via a plug 386. Therefore, a plug (386) with a cable (387) is arranged in the receptacle (382) in order to be connected to the cartridge.

Figure 12:
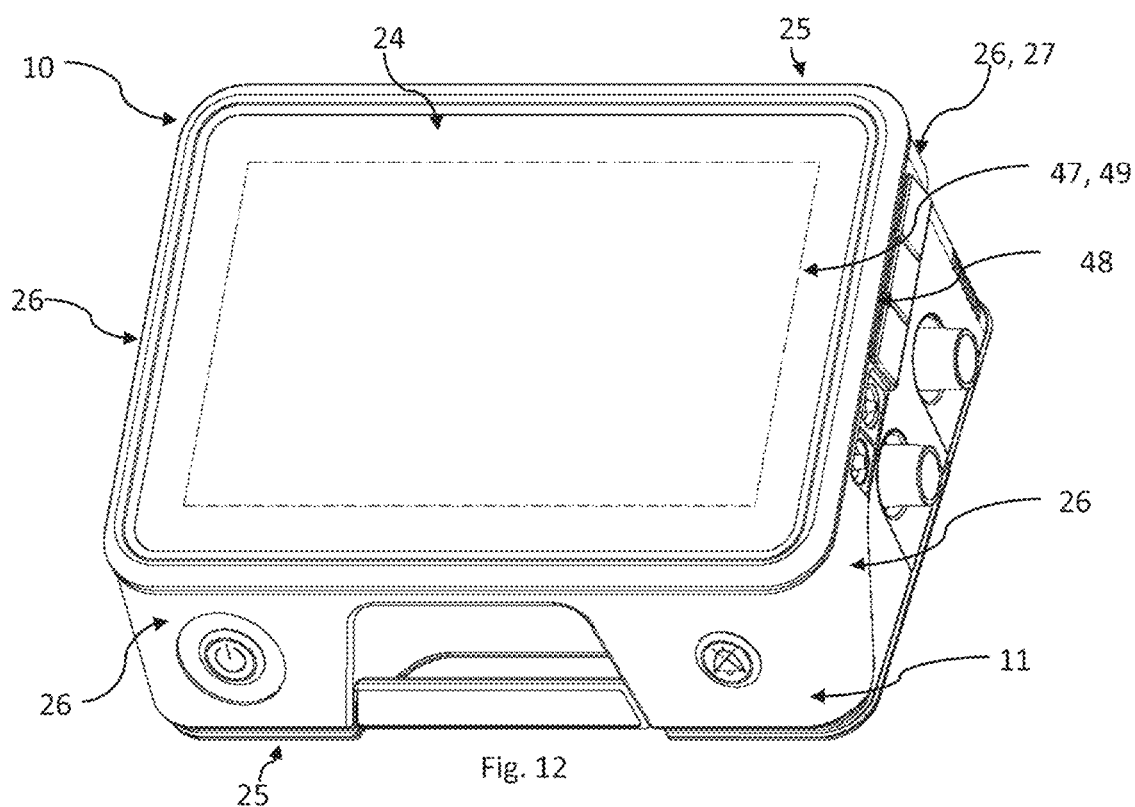
FIG. 12 shows a detail of a user interface of the device according to the invention.

FIG. 12 shows a detail of a user interface 47 of the device 10 according to the invention. The device 10 comprises the user interface 47, which is designed as a GUI. The user interface 47 is arranged flat in the top wall 24 of the housing 11. The diagonal (or the length of the diagonal) of the user interface 47 is greater than 70%, preferably greater than 75%, of the diagonal of the housing surface in which the user interface 47 is arranged.

The user interface 47 is configured to show a display/image corresponding to a selected bottom wall 25. Both the bottom wall 25 and a side wall 26, which is configured as optional bottom wall 27, can thus determine the orientation of the display/image of the device 10. According to the respectively selected bottom wall 25, the device 10 automatically adapts the orientation of the display/image. The GUI is generally a touch screen. Optionally, the device can comprise haptic operating elements. For example, haptic rotary elements can be arranged on at least one of the side walls 26.

What is claimed is:

1. A respiratory device, wherein the respiratory device comprises a housing, a user interface, and a pneumatic unit; the pneumatic unit comprising at least one of each of a respiratory gas drive, a measuring unit, a control unit, and a sound unit; the pneumatic unit being designed as a pneumatic conveying line which forms a respiratory gas path from an appliance inlet to an appliance outlet of the housing, and at least one component of the pneumatic unit or the pneumatic conveying line being removable from the housing, and wherein a cooling air path driven by a cooling fan is guided through the housing from a cooling air inlet to a cooling air outlet and at least the control unit, the respiratory gas drive and a main circuit board are arranged in the cooling air path in such a way that the component having the highest heat build-up during operation is arranged at an end of the cooling air path in a direction of flow of the cooling air path wherein the component having the highest heat buildup is at least one of the control unit, the respiratory gas drive, and a main circuit board.

2. The respiratory device of claim 1, wherein the pneumatic unit is designed as the pneumatic conveying line which is formed and arranged from the appliance inlet to the appliance outlet of the housing and comprises a support frame on which at least one component selected from the respiratory gas drive, the sound unit, a flow measurement path, the measuring unit and the cooling fan is arranged, the pneumatic conveying line being removable from the housing.

3. The respiratory device of claim 1, wherein the pneumatic conveying line is mounted in the housing of the device by at least one viscoelastic or elastomeric suspension.

4. The respiratory device of claim 1, wherein the respiratory gas path through the housing is pneumatically separate from the cooling air path through the housing and/or the appliance inlet is arranged in the housing in a manner spaced apart from the cooling air outlet in such a way that no air is aspirated through the appliance inlet from the cooling air outlet.

5. The respiratory device of claim 1, wherein the housing comprises a top wall, at least one bottom wall and at least two side walls, the appliance inlet and the appliance outlet being formed on two non-opposite side walls of the housing.

6. The respiratory device of claim 5, wherein at least one side wall is configured as a bottom wall.

7. The respiratory device of claim 5, wherein the bottom wall of the housing is detachable, and the pneumatic conveying line is removable in one piece via an opening of the bottom wall.

8. The respiratory device of claim 5, wherein an accumulator and the respiratory gas drive are arranged in the housing in such a way that, in an orientation of the device both on the bottom wall and also on a side wall configured as bottom wall, a center of gravity is formed by the accumulator and the respiratory gas drive.

9. The respiratory device of claim 5, wherein no cooling air inlet or cooling air outlet is arranged in the bottom wall or in a side wall configured as bottom wall.

10. The respiratory device of claim 1, wherein the pneumatic conveying line comprises at least two sound units, at least one sound unit being arranged on a suction side of the pneumatic conveying line and one sound unit being arranged on a pressure side of the pneumatic conveying line.

11. The respiratory device of claim 10, wherein the at least one sound unit on the suction side is arranged at a receptacle of the respiratory gas drive and comprises a blower cap, a foam carrier, at least one absorber foam, a decoupling device and at least one foam ring.

12. The respiratory device of claim 1, wherein the respiratory gas drive is arranged at the end of the cooling air path in the direction of flow of the cooling air path.

13. The respiratory device of claim 1, wherein the cooling air path is designed and configured in an opposite direction to and independent of the respiratory gas path of the pneumatic conveying line.

14. The respiratory device of claim 1, wherein the pneumatic unit further comprises a flow measurement path which comprises at least one flow measuring unit and is configured to detect at least one parameter of a respiratory gas in the flow measurement path, the flow measurement path being designed and configured linearly, a lattice mesh being arranged at a start and/or at an end of the flow measurement path, and being designed to be removable and reconditionable.

15. The respiratory device of claim 14, wherein the at least one flow measuring unit is designed and configured to be removable from the housing and comprises at least one sensor for detecting at least one parameter of the respiratory air guided via the respiratory gas path.

16. The respiratory device of claim 1, wherein the device comprises a receptacle for a quick-change adapter and comprises the quick-change adapter which is connected to a support frame via a rotary element, the quick-change adapter being configured to be pivotable in the receptacle from a first position to a second position via a rotation axis of the rotary element, the quick-change adapter in the second position being pivoted out from the receptacle such that in the second position a receptacle for an O2 cartridge is accessible and an O2 cartridge can be inserted, and wherein the quick-change adapter can then be pivoted back into the receptacle, together with the O2 cartridge, to the first position.

* * * * *